United States Patent [19]
Holmlund et al.

[11] 3,984,708
[45] Oct. 5, 1976

[54] ELECTROMAGNETIC TACTILE STIMULATOR
[75] Inventors: Gordon Wayne Holmlund, Oakland; Albert Barry Alden, San Francisco, both of Calif.
[73] Assignee: The Institutes of Medical Sciences, San Francisco, Calif.
[22] Filed: Sept. 11, 1975
[21] Appl. No.: 612,424

[52] U.S. Cl. .................................. 310/30; 128/41; 340/407
[51] Int. Cl.² ...................................... H02K 33/06
[58] Field of Search ..................... 340/407; 128/41; 310/18, 30, 34, 35, 23, 17, 19

[56] References Cited
UNITED STATES PATENTS

| | | |
|---|---|---|
| 1,999,795 | 4/1935 | Wright ......................... 128/41 UX |
| 2,441,686 | 5/1948 | Cohen ............................... 128/41 |
| 2,690,547 | 9/1954 | Marks et al. ................... 340/407 X |
| 2,726,342 | 12/1955 | Cavetto .............................. 310/30 |
| 3,149,255 | 9/1964 | Trench ............................... 310/30 |
| 3,184,622 | 5/1965 | Levine ................................ 310/30 |

Primary Examiner—Donovan F. Duggan
Attorney, Agent, or Firm—Townsend and Townsend

[57] ABSTRACT

An improved electromagnetic tactile stimulator is disclosed for preferable use in a matrix array. A plurality of such stimulators are confronted to impart vibratory impulses of varying intensity to the skin of a subject to augment typically lost sensual modality such as sight or sound. Each electromagnetic tactile stimulator is in the form of a solenoid having a magnetically polarized plunger.

7 Claims, 9 Drawing Figures

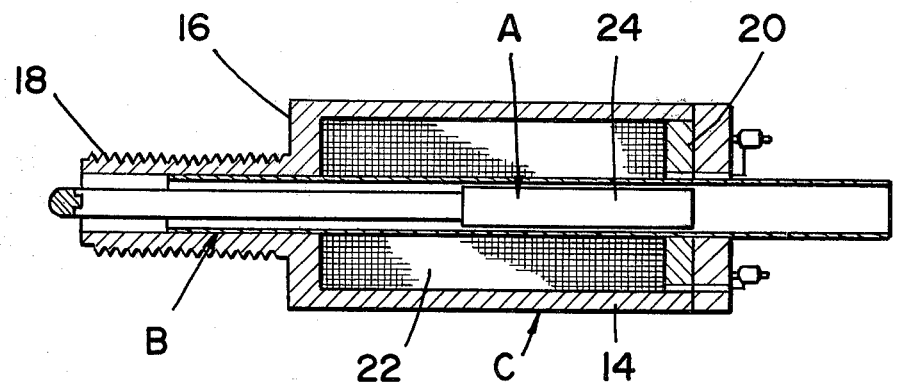
FIG_1 (PRIOR ART)
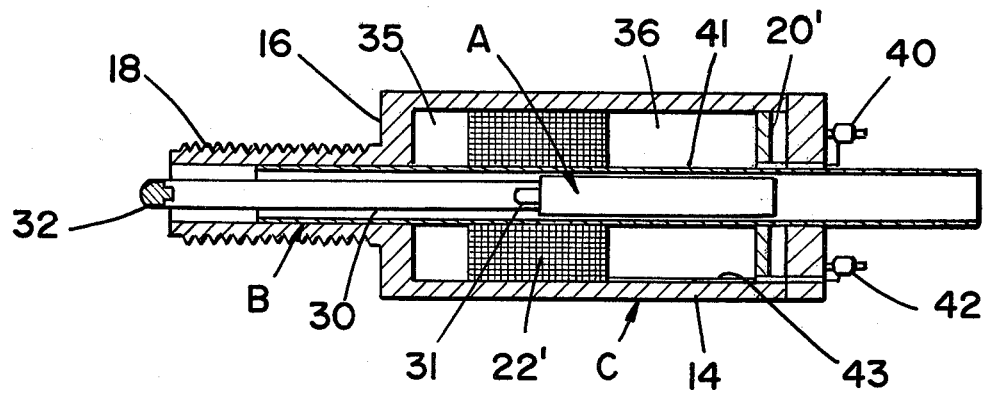
FIG_2
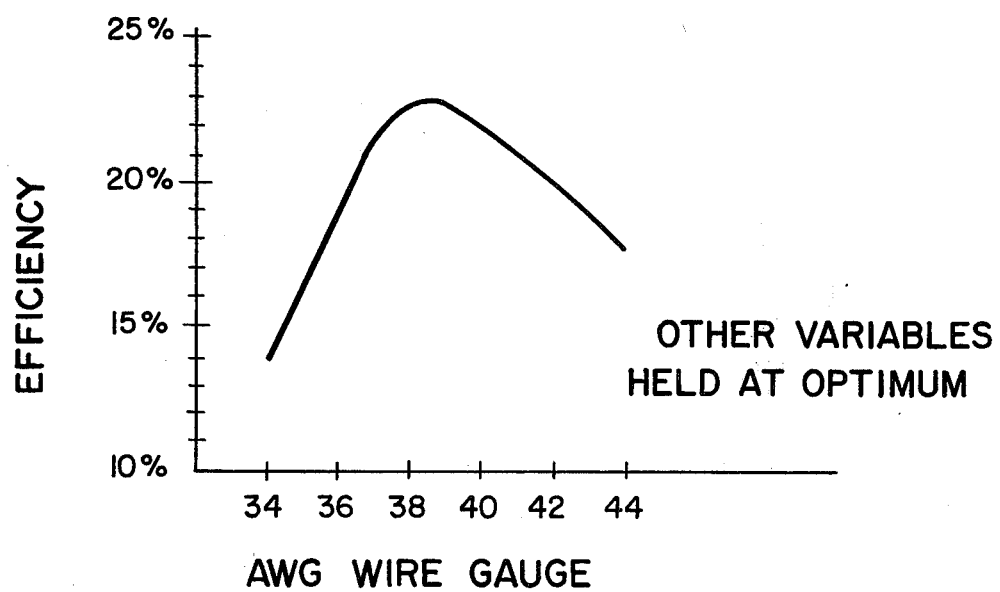
FIG_6

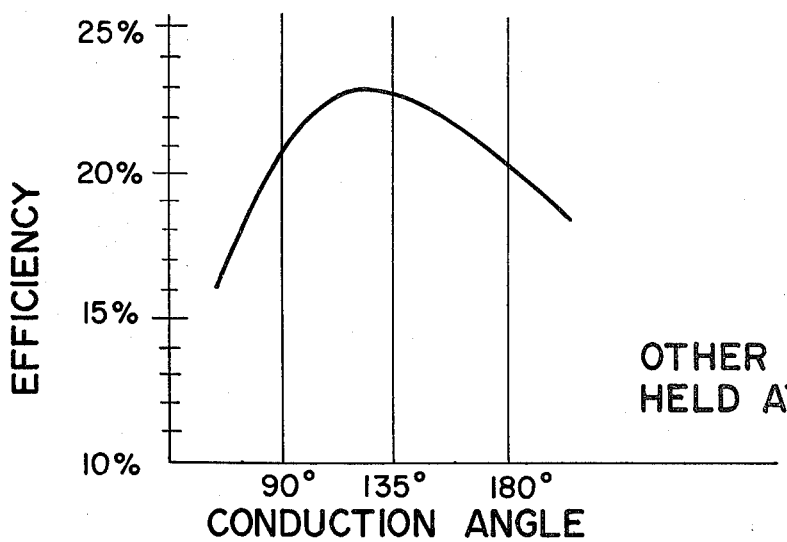
FIG_7 OTHER VARIABLES HELD AT OPTIMUM
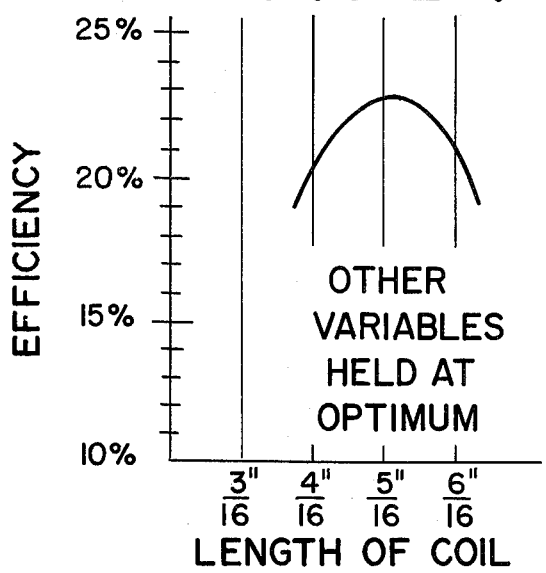
FIG_4
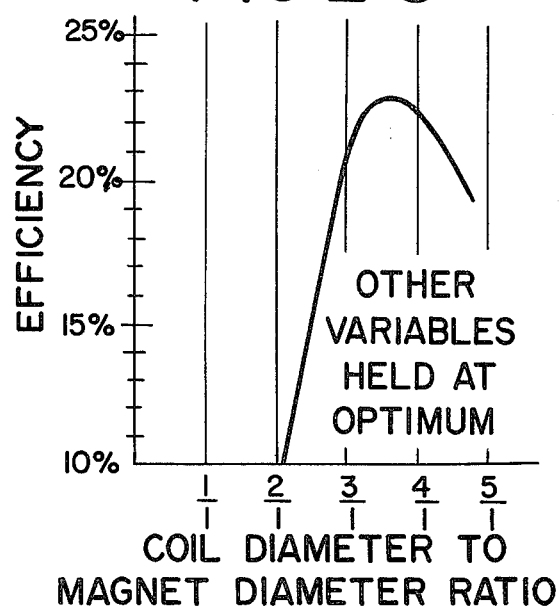
FIG_3
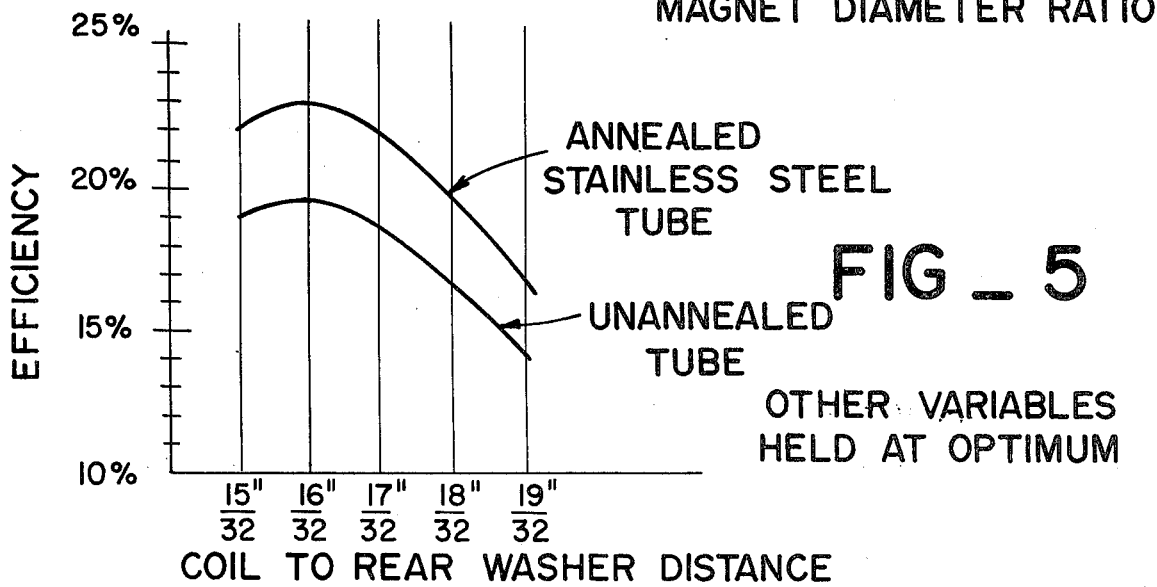
FIG_5

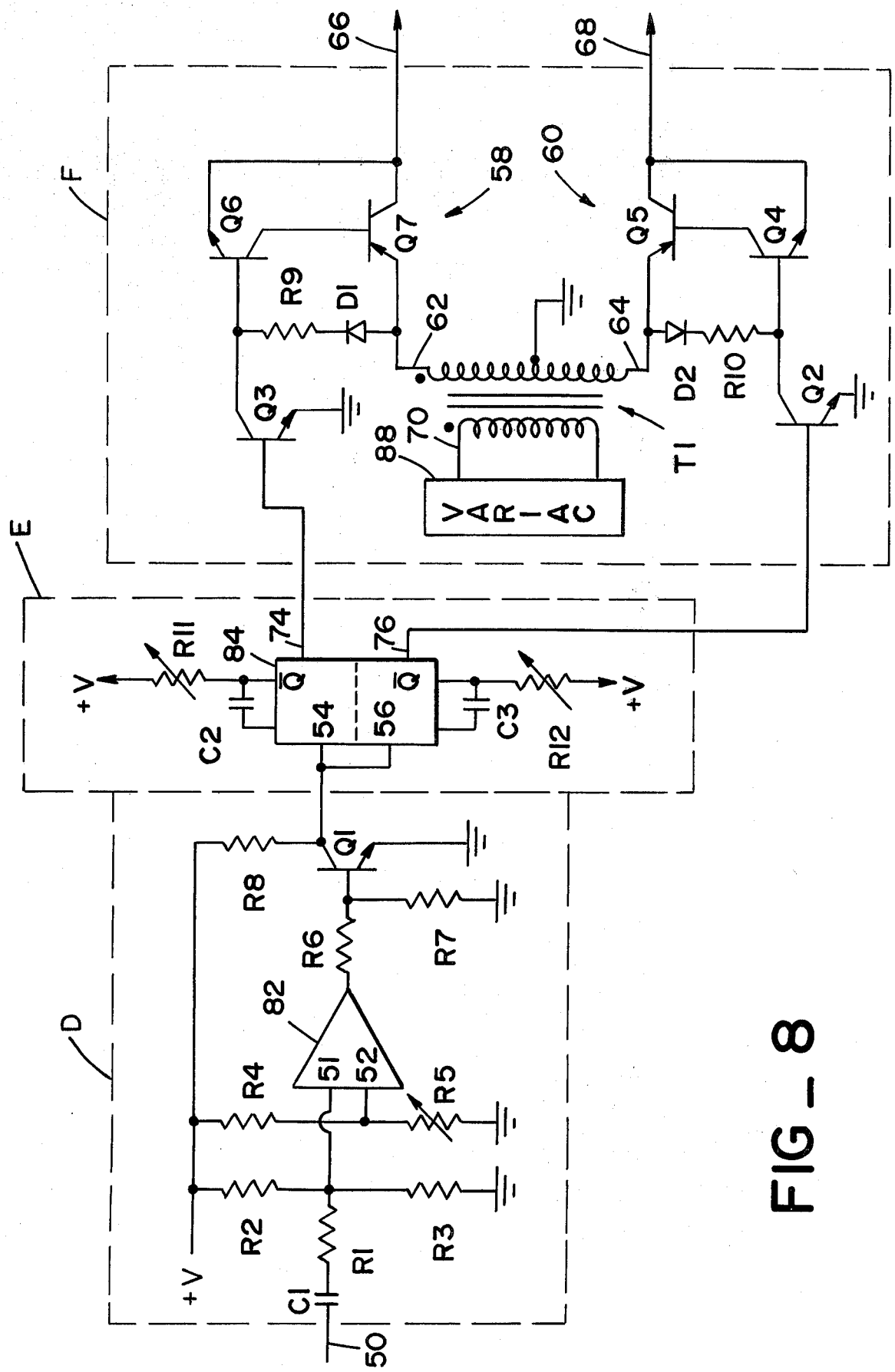
FIG_8

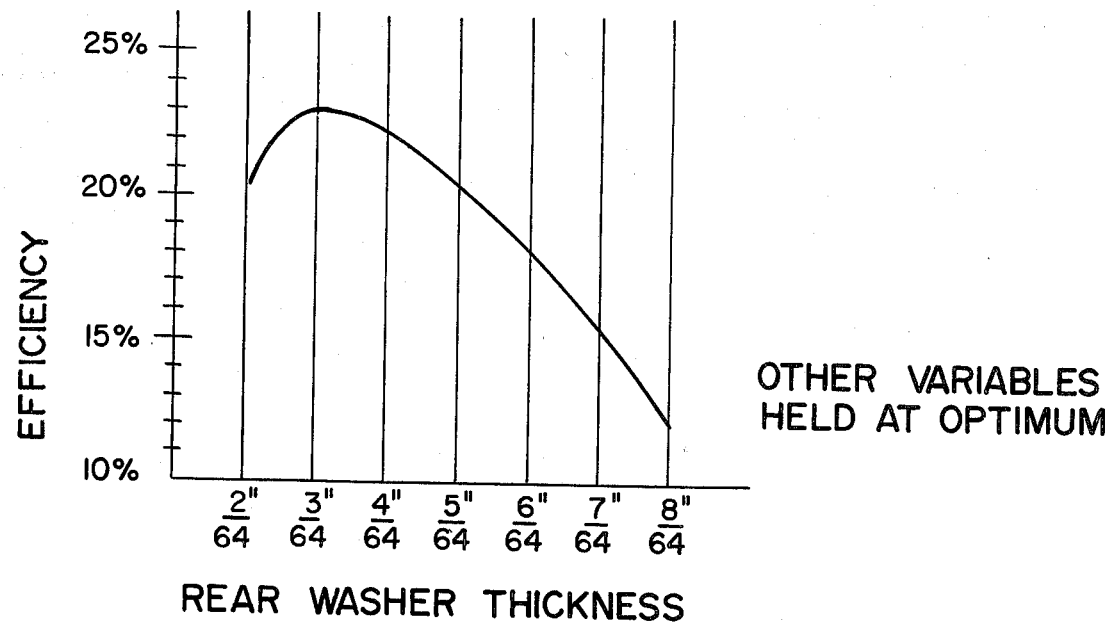
FIG_9

ELECTROMAGNETIC TACTILE STIMULATOR

The invention described herein was made in the course of work under a grant for award from The Department of Health, Education and Welfare.

This invention relates to solenoids and, more particularly, to solenoids of the type wherein a tactile stimulator contacts the flesh of a subject having lost sensory modality and, through stimulation of the flesh, typically in an array, augments typically lost sensory modality.

SUMMARY OF THE PRIOR ART

An electromagnetic tactile stimulator has been described in a publication entitled "An Electromagnetic Tactile Stimulator" by Gordon Wayne Holmlund and Carter Compton Collins, and is illustrated and described in the attached drawings. In this prior art, the wound coil was coincident with the full length of the inside of the high permeability, toroidal, magnetic loop of the solenoid and was described as required to be longer than the magnetic plunger. Low output efficiency in the order of 3.4% resulted.

It has always been desirable to reduce in size the diameter of such a solenoid. With this reduction in diameter, the force available for tactile stimulation was reduced. Reduction of output force to the point where tactile stimulation could occur at all was lost.

Moreover, such units were of low efficiency. Relatively high power requirements were necessary, making portable power sources not practicable. Moreover, the heat losses over prolonged use caused arrays in which the stimulators were mounted to become hot to the point where they were not only uncomfortable, but could no longer be worn.

Attempts to produce solenoids with unpolarized iron cores were made. Such soft iron core units have noise when the air gap between the high permeability path and core is closed. To prevent noise, it is required that such non-polarized core units operate at all times with some amount of air gap. Unfortunately, output energy falls off rapidly with the production of air gap because of the great increase in the reluctance of the magnetic loop. Moreover, with an air gap maximum energy can never be realized. To approach maximum energy, the plunger must be located at a precise point which is as close as practical to closing of the air gap and yet is sufficiently removed to prevent noise. Typically, a spring restoring system must be established with this as a starting point.

NATURE OF THE PROBLEM

After much experimentation, we have established parameters for electromagnetic tactile stimulators. Such stimulators must have an available energy output in the order of 32 milliwatts and must be variable in output as a function of the current input. Preferably, the solenoids must have as small an overall diameter as possible so that when they are mounted in an array, their tactile stimulators may be dense enough for mounting to parts of the body having high tactile resolution. It is preferred to have high electromagnetic efficiency to produce as low a heat output as possible with minimum power. Finally, it is preferred to have the mode of resonance when coupled with the human skin to produce maximum output in the range of 50Hz to 60Hz to make the system compatible with the alternating frequencies of most world power sources.

SUMMARY OF THE INVENTION

An improved electromagnetic tactile stimulator is disclosed for preferable use in a matrix array. A plurality of such stimulators are confronted to impart vibratory impulses of varying intensity to the skin of a subject to augment typically lost sensual modality such as sight or sound. Each electromagnetic tactile stimulator is in the form of a solenoid having a magnetically polarized plunger. The plunger is mounted interior of a nonmagnetic stainless steel sleeve. The excursion of the plunger varies with respect to a toroidal, high permeability path for a coil induced magnetic field. The high permeability path of the field is confined within the sleeve at the inside of the toroid, confined within an outer sleeve at the outside of the toroid, and is limited at either end between the sleeves by washers. The magnetized portion of the plunger is at least six times as long as its diameter, mounted for a sliding reciprocal fit interior of the inside sleeve, and has a length approximately three quarters as long as the interior of the toroid. A winding about the sleeve of enamel type insulated copper wire extends for approximately 5/16 of the length of the high permeability path between the front and rear washer towards the front washer of the solenoid. In the absence of current communicated to the windings of the coil, the plunger assumes a normal position adjacent the rear washer of the solenoid. When the solenoid is powered by half wave rectified current lopped off at 112° of the cycle, the polarized plunger with attached tactile stimulating tip has a seven-fold increase in solenoid efficiency from 3.4% in prior art to 22.9% in overall output.

OBJECTS AND ADVANTAGES OF THE INVENTION

An object of this invention is to improve the output efficiency of a tactile stimulator. According to this aspect of the invention, the coil windings of the stimulator are reduced to 5/16 of the internal path of the high permeability magnetic loop and established with the center windings of the coil at a 21/32 spacing from the rear washer of the loop towards the front washer of the loop.

An advantage of this coil length reduction and coil length spacing is that a seven-fold increase in solenoid efficiency results. Smaller solenoids can be made to produce the required 32 milliwatt output. A denser array of such solenoids can result.

Yet another object of this invention is to disclose a preferred half wave rectified wave pattern for powering the solenoids to realize maximum loaded output of the solenoid. According to this aspect of the invention, the solenoid is powered by half wave rectified current with the half wave lopped off at 112° of the cycle.

An advantage of the solenoid of this invention coupled with such an improved power source is that maximum output with minimum power input and heat loss results.

Other objects, features and advantages of this invention will become more apparent after referring to the following specification and attached drawings in which:

FIG. 1 is a description of a prior art electromagnetic tactile stimulator described in the Holmlund-Collins article;

FIG. 2 is a drawing of the preferred embodiment of the solenoid according to this invention;

FIG. 3 illustrates graphically the change in overall efficiency in response to varying the coil diameter to magnet diameter ratio;

FIGS. 4-5 illustrate graphically the change in overall efficiency in response to varying the length of the coil and coil to rear washer distance, respectively;

FIG. 6 illustrates graphically the change in overall efficiency in response to selection of different AWG wire gauge;

FIG. 7 illustrates graphically the change in overall efficiency in response to varying the conduction angle;

FIG. 8 is a schematic representation of a stimulator power source that provides the preferred 112° positive half-wave of a 60Hz sine wave; and FIG. 9 illustrates the change in solenoid efficiency as the thickness of the rear washer is varied.

The invention herein set forth can be best understood by explaining first the toroidal, high permeability, magnetic path common to both the prior art and present solenoid. Thereafter, the improved efficiency of the solenoid of this invention can be discussed with respect to the polarized magnetic plunger, the wound coil of reduced length, and the optimum location of the solenoid interior of the high permeability path.

Referring to FIGS. 1 and 2, a cylindrical solenoid is shown in section. A magnetic plunger A is mounted interior of a stainless steel sleeve B. Sleeve B is in turn mounted for a force friction fit interior of a cup assembly C having outside wall 14, front washer wall 16, and protruding mounting threads 18. In the case of both the prior art and the instant invention, an end wall for washer 20 is mounted between tubing B and the inside of wall 14 of the cup assembly C at the rear open end of cup assembly C.

Having gone this far, the high permeability path provided is toroidal in shape. That is to say, it is that figure generated by a closed loop revolved in space. In this case, the loop comprises the side wall of tubing B at the inside, wall 14 of cup assembly C at the outside, closed by washer 16 at the front end, and washer 20 at the rear end. Electromagnetic field is essentially confined to the high permeability path provided.

It will be noted that the toroidal, high permeability path is twice as long as its diameter.

Length to diameter ratio of a permanent magnet determines the amount of Residual Induction ($B_r$) retained after being magnetized. The choice of this ratio, therefore, depends upon the characteristics of the material with allowance for demagnetization in the magnetic circuit in which it is used. Preferably, magnetic plunger A is constructed from Alnico 5, the most practical material (cost/$B_r$) at the present state of the art and commerically available from many magnet manufacturers. The preferable length to diameter ratio of magnetic plunger A using Alnico 5 is 6 to 1. The resulting parameters of the magnet will then determine the optimum value of all other dimensions of the stimulator solenoid.

Additionally, it is known, with respect to the two pole pieces or washers 16 and 20, that their separation had to be longer than the magnet itself. This was to permit the plunger to have appreciable excursion.

Moreover, it was found desirable that the ratio of coil diameter to magnet diameter be approximately 3.5:1 (see FIG. 3).

However, it was not known in the prior art what effect varying the thickness of the rear pole piece would have, if any, on the output of the type of stimulator presented here. The rear washer 20 to which the magnet A is attracted during the time current is not applied to coil 22, provides a restoring pull for the magnet. Since the solenoid operates in a vibratory mode, there will exist an optimum value of pull to return magnet A to a normal position adjacent the rear washer 20 in the interval of time before the next application of current to coil 22. It was found that by varying the thickness of the rear washer 20 an optimum value of pull can be obtained when operating the solenoid at 60Hz. This is shown in FIG. 9, which illustrates the overall increase in efficiency of a solenoid using an Alnico 5 magnet obtained when the rear washer thickness was varied from 8/64 inch to 3/64 inch. As can be seen, overall efficiency was increased from approximately 13% to 23%.

Referring to FIG. 1, the differences between the present solenoid and the prior art can be emphasized. First, as to the coil 22, this coil consisted of number 40 enamel, insulated layer or universal wound coil interior of the cup assembly C along the full length of the volume therein provided defined by front washer wall 16 and washer 20. This cup assembly was longer than the polarized portion 24 of the plunger A. Moreover, stainless steel tube B was unannealed and typically contained residual magnetism resulting from processes of manufacture. When this stimulator was provided with half wave current, an overall efficiency in the order of 3.4% was generated.

Referring to FIG. 2, the improved solenoid of this invention is illustrated. Coil 22' is wound to have a preferred length, suggested by the experimental results depicted by FIG. 4, equal to 5/16 of the length between front washer 16 and rear washer 20'. This winding can range from 4/16 to 6/16 of the length of the interior of the provided toroidal, high permeability path. The windings of the coil 22' of a solenoid with a cup assembly C having an outside diameter of ½ inch preferably constitute number 38 enamel type insulated wire, as suggested by FIG. 6. A solenoid with a ¼ inch outside diameter for cup assembly C will preferably use number 40 enamel type insulated wire.

Moreover, the spacing from the rear washer 20' of this coil of improved length has proved to be critical, as FIG. 5 suggests. The center of the winding of winding 22' is spaced at an interval 21/32 from rear washer 20' towards the front washer 16. It has been found that a 1/32 movement of the coil 22' towards, or away from, the rear washer 20' produces a 1% drop in overall efficiency. Thus, the position of the coil of reduced length has been found to be surprisingly critical.

At the preferred location of the coil, length changes in the coil likewise produce changes in efficiency, as FIG. 4 illustrates. For example, if the coil is 6/16 of the length of the toroid, an efficiency of 20.5% for an overall efficiency drop of 2.5% results.

Returning to the description of the magnetic plunger A, a stainless steel tube 30 is typically mounted to the forward portion of the magnet A at a forced fit 31 adjacent the magnet. It protrudes outwardly from the magnet and terminates in a tactile stimulator tip 32 which preferably can be a piece of semispherical Teflon force fitted interior of the tip of supporting tube 30. Preferably, magnet A is mounted interior of the tube B and is not lubricated. It has been found that over a period of time virtually any lubricant wears off or disadvantageously becomes contaminated to cause a greater friction than the clean metal on metal coefficient of friction.

To provide for precise spacing of the reduced winding 22', two dielectric spacers are provided. A spacer 35 abuts washer at the inside of the cup assembly C. A second spacer 36 abuts the completed coil adjacent the rear washer 20'. These respective spacers give the required, precise positioning of the coil 22'.

Powering of the solenoid occurs from a first terminal 40 through a communicating wire 41 to the inside of coil 22'. This circuit to the coil is completed at a terminal 42 through a wire 43 to the outside of the coil 22'.

It has been found, as FIG. 7 illustrates, that it is preferable to power the coil with a half wave rectified current lopped off at 112° of the half wave alternating current.

A preferred circuit for providing a number of solenoids with 112° half wave alternating current is shown in FIG. 8. Generally designated within the dotted lines of FIG. 8, are a zero crossing detector D, a variable pulse generating circuit E, and gated stimulator power source F. A small AC 60Hz sine wave from variac 18 is coupled to terminal 50 of zero crossing detector D. This sine wave is coupled, by capacitor C1, to input 51 of operational amplifier 82. Resistors R1, R2 and R3 determine the peak to peak value of the signal to appear at input 51. Additionally, resistors R2 and R3 form a voltage divider that cause the 60Hz sine wave at input 51 to vary about some DC voltage. Resistors R4 and R5 form another voltage divider network that present a DC voltage to input 52. Operational amplifier 82 is used as a comparator such that whenever input 51 becomes negative with respect to input 52 the output of the operational amplifier 12 will experience a voltage transition from a positive to a zero or ground voltage level.

This positive to ground transition is coupled to dual one-shot 84 of pulse generating circuit E, via the buffer circuit comprising resistors R6, R7, R8 and transistor Q8, as a zero to positive voltage transition. Dual one-shot 84 is typically an SN 74123 commercially manufactured by Texas Instruments. Receipt of a negative to positive transition by inputs 54, 56 of dual one-shot 84 will cause outputs 72, 74, which are the $\bar{Q}$ outputs, to become an approximately zero voltage for a period of time determined by their respective timing networks R11, C2 and R12, C3. Resistors R11 and R12 are variable resistors and are present to determine the period of time outputs 74 and 76 remain at approximately zero voltage, after the positive-going voltage transition at inputs 54, 56. After the timing networks R11, C2 and R12, C3 time out, the outputs 74, 76 return to a positive voltage.

Outputs 74, 76 provide the gating pulses used to gate portions of positive half waves of 60Hz sine wave when coupled to stimulator power source F. Power source F consists of gate 58 which supplies gated half-wave power to one-half of an array of stimulators via lead 66 while gate 60 supplies the remainder via lead 68. Gates 58 and 60 operate in identical manner to gate a portion of the half wave alternating current, preferably 112°, so that a description of gate 58 will apply also to gate 60.

When output 74 of dual one-shot 84 is positive, transistor Q3 is in a conducting state which effectively causes the base of Q6 to be at ground potential. Thus, Q6 is non-conducting or off state, which in turn, holds pass transistor Q7 in an off condition. Any voltage appearing at terminal 62 of the secondary of transformer T1 is blocked from appearing at output lead 66. When dual one-shot output 74 becomes a zero or ground potential, Q3 ceases to conduct. When terminal 62 of transformer T1 is positive, the base of Q6 will achieve a positive potential via the biasing network of diode D1 and resistor R9. Q6 will then be capable of conducting but, as can be seen, only when terminal 62 of the transformer T1 is positive. With Q6 able to conduct, Q7 can also conduct. Thus, voltage at terminal 62 will be passed to output lead 66 only if positive and only when dual one-shot output 74 is at zero or ground potential.

The circuit action of gate 60 is identical. Transistor Q5 will pass the voltage at terminal 64 of transformer T1 to output lead 68 only when terminal 68 is positive and dual one-shot output 76 is at zero or ground potential.

In operation, therefore, a positive-going voltage transition is coupled to inputs 54, 56 of dual one-shot 84 when the signal appearing at input terminal 50 (which has the same phase relationship with primary terminal 70 of transformer T1) of detector A passes through zero voltage in a negative direction. At this point in time, the voltage appearing at transformer terminal 62 begins the negative half-cycle excursion. Properly presetting variable resistor R12 so that output 76 of dual one-shot 84 remains at ground potential for a time equal to 112° of the positive half-cycle of the 60Hz sine wave appearing on terminal 64. Similarly, variable resistor R11 must be set so that output 74 remains at ground potential for a time equal to 292° of a 60Hz sine wave (180° plus 112°) so that only 112° of the positive half-wave will appear upon lead 66.

When the solenoid coil has no current applied, magnet A rests in the position shown in FIG. 2. When current is applied, permanent magnet A advances towards washer 16. Resistance to this advance by the skin produces the required power output.

It should be noted that the half wave current provided coil 22' produces vibration of the magnetic plunger A and imparts this to the stimulator tip 32. This vibration results in tactile input being perceptible at stimulator tip 32.

We have constructed two models of the instant invention. In a first model the outside diameter of the cup assembly C has been in the order of half an inch. In a second model the outside diameter of the cup assembly C has been in the order of one quarter of an inch. It should be noted, however, that some compromise in effieciency in the one quarter inch unit was required to attain an output power of 32 milliwatts or better. Maintaining the coil diameter to magnet diameter ratio of 3.5:1, as suggested by FIG. 3, to obtain maximum efficiency resulted in an output power of approximately 17% for the quarter inch unit. The reason being that output power is determined, in part, by the energy of the magnet which, in turn, depends upon magnet size. Thus, to increase power output, the magnet diameter of the quarter inch unit was increased. The resulting coil diameter to magnet diameter ratio of approximately 2.6:1 provided a lower efficiency, but an output power of at least 32 milliwatts. The dimensions of these models are summarized in the following table:

| PART | ½" DIAMETER SOLENOID | ¼" DIAMETER SOLENOID |
|---|---|---|
| Cup Assembly C | | |
| Outside Diameter | .500" | .250" |
| Cup Assembly C | | |
| Inside Diameter | .454" | .234" |
| Cup Assembly C | | |
| Washer 16 | | |
| Thickness | .125" | .0937" |
| Washer 20 | | |
| Thickness | .0468" | .0937" |
| Magnet Plunger A | | |
| Length | .750" | .5625" |
| Diameter | .131" | .091" |
| Stainless Steel Tip B | | |
| Supporting Tube 30 | | |
| Length | 1.125" | .5781" |
| I.D. | .063" | .056" |
| O.D. | .083" | .072" |
| Stainless Steel Guide | | |
| Tube B | | |
| Length | 2.125" | 1.3125" |
| I.D. | .136" | .094" |
| O.D. | .166" | .120" |
| Coil 22' | | |
| I.D. | .166" | .120" |
| O.D. | .454" | .234" |
| Wire Size | 38 | 40 |
| No. of turns (approx.) | 2300 | 1300 |
| Length | .3125" | .2812" |
| Output Power Mechanical | | |
| (Maximum) | approx. 160 mw | 40 mw |
| Center of coil 22' | | |
| to rear washer 20 | | |
| Distance | .6562" | .4844" |

It will be appreciated that before the improvement in overall efficiency set forth herein, the construction of a quarter inch diameter solenoid for tactile imaging purposes was not practical. The resulting output power was sufficiently below 32 milliwatts so as to make a useful array image not capable of accepting a required amount of intensity variation to impart reasonable image resolution.

We claim:

1. An improved electromagnetic tactile stimulator comprising means for defining a toroidal, high permeability, magnetic field including an inner sleeve, an outer sleeve, and forward and rear disk shaped walls extending between said sleeves to define interior of said sleeves and walls a toroidal, high permeability path; a plunger magnetically polarized having an external diameter for a freely moving fit interior of said inner sleeve defining the inside portion of said toroidal, high permeability path and having a longitudinal length to the external diameter ratio of 6:1; a winding of wire interior of said toroid between said disks having a length in the range of 4/16 to 6/16 of the length between said disks wth the center wind of said winding positioned in the range between 20/32 and 22/32 from said rear disk to said forward disk; and, a stimulator tip attached to said permanent magnet in coaxial relationship to protrude outwardly from said polarized magnetic core of said stimulator to impart stimulating mechanical vibrations for tactile perception of a subject.

2. The invention of claim 1 and wherein said toroidal, high permeability path is twice as long between said disk shaped walls as it is between the walls of said outer sleeve.

3. The invention of claim 1 and wherein said winding has a length of 5/16 of the length between said disks.

4. The invention of claim 1 and wherein the center wind of said winding is positioned at 21/32 the distance from said rear disk to said forward disk.

5. An improved electromagnetic tactile stimulator comprising means for defining a toroidal, high permeability, magnetic field including an inner sleeve, an outer sleeve, and forward and rear disk-shaped walls extending between said sleeve to define interior of said sleeves and walls a toroidal, high permeability path; a permanently magnetized magnet having a length and an external diameter the ratio of which is 6:1 movably situated interior said inner sleeve; a stimulator tip attached to said permanent magnet in coaxial relationship to protrude outwardly from said polarized magnetic core of said stimulator to impart stimulating magnetic vibrations for tactile perception of a subject; a winding of wire interior of said toroid between said disks having the length of 4/16 to 6/16 of the length between said disk with the center wind of said winding positioned in the range between 20/32 and 22/32 from said rear disk to said forward disk; and, means for generating a half wave, rectified current, said half wave, rectified current interrupted between 102° and 122°.

6. The invention of claim 5 and wherein said rear disk is adjusted in mass with respect to said magnetically polarized plunger to resonate in the range of 50Hz to 60Hz when said stimulator tip is contacted with said human skin.

7. The invention of claim 5 and wherein said half wave, rectified current is lopped off at 112°.

* * * * *